United States Patent [19]

Estis et al.

[11] Patent Number: 4,680,175

[45] Date of Patent: Jul. 14, 1987

[54] INTERFERON ADMINISTRATION VEHICLES

[75] Inventors: Leonard F. Estis, North Brunswick; Sean A. Evans, High Bridge; Douglas Testa, Neshanic Sta., all of N.J.

[73] Assignee: Interferon Sciences, Inc., New York, N.Y.

[21] Appl. No.: 577,911

[22] Filed: Feb. 7, 1984

[51] Int. Cl.$^4$ .................. A61K 45/02; A61K 31/745
[52] U.S. Cl. ......................................... 424/85; 424/83
[58] Field of Search ..................... 424/83, 85; 514/781

[56] References Cited

U.S. PATENT DOCUMENTS

| | | | |
|---|---|---|---|
| 4,348,384 | 9/1982 | Horikoshi et al. | 424/101 |
| 4,478,822 | 10/1984 | Haslam et al. | 424/85 |
| 4,507,281 | 3/1985 | Asculai et al. | 435/68 |

FOREIGN PATENT DOCUMENTS

83/01198  4/1983  PCT Int'l Appl. .

OTHER PUBLICATIONS

*Remington's Pharmaceutical Sciences*, 15th Ed., (Arthur Osol, Ed.), Mack Pub. Co., Easton, PA, 1975, pp. 1243-1253.

Mihalyi, E., *Appl. of Proteolytic Enzymes to Protein Structure Studies* vol. 1, 2d ed, CRC Press, Boca Raton, FL, 1978, pp. 43-54 and 114-127.

Moller et al., Third Annual International Congress for Interferon Research, 1982.

*Primary Examiner*—Blondel Hazel
*Attorney, Agent, or Firm*—Vincent P. Pirri

[57] ABSTRACT

An interferon preparation to be administered topically is provided comprising: (a) a therapeutically effective amount of one or more interferons; (b) a vehicle base compatible with the interferon or interferons being administered; (c) an effective amount of one or more protease inhibitors for the purpose of reducing the rate of decay of the biological activity of the interferon or interferons due to proteolytic agents; and (d) an effective amount of one or more anti-microbial agents. In certain preferred embodiments of the invention, the vehicle base is prepared from a mixture of polyethylene glycols or includes hydroxyethyl cellulose as a thickening agent.

11 Claims, 2 Drawing Figures

Figure 2

INTERFERON ADMINISTRATION VEHICLES

BACKGROUND OF THE INVENTION

1. Field of the Invention

This invention relates to interferon and in particular to vehicles for the topical and local administration of interferon.

2. Description of the Prior Art

In 1957, Isaacs and Lindenmann observed that supernatant fluids from virus-infected cell cultures contained an activity which could protect normal cells against infection by a wide variety of viruses. This activity was associated with a protein component which they called "interferon". Subsequently, it has been shown that there are various distinct types of interferon, generally classified as $\alpha$, $\beta$ and $\gamma$ interferons, which possess not only anti-viral activity, but also potent anti-cellular, anti-tumor and immunoregulatory activities.

$\alpha$ and $\beta$ interferons, also known as Type I interferons, are induced by viruses or synthetic polynucleotides acting on leukocyte and fibroblast cells, respectively. $\gamma$-interferon, also known as immune or Type II interferon, is induced in primed lymphocytes by specific antigens or in unprimed lymphocytes by T-cell mitogens. All of these interferons have proved extremely difficult to purify to homogeneity and as a consequence are most often used as crude or partially purified preparations. General discussions of these interferons can be found in various texts and monographs, including *The Interferon System*, by W. E. Stewart, II, Springer-Verlag, New York (1979); *Interferon* 1981, Vol. 3, edited by Ion Gresser, Academic Press, New York (1981); and *Interferon Therapy*, World Health Organization Technical Reports Series 676, World Health Organization, Geneva, 1982.

For over a decade, interferons of all types have been employed in clinical trials. Originally, they were applied against viral pathogens, but subsequently their use has been extended to include treatment of a variety of malignant diseases. An important factor in the clinical application of interferons is the method of administration. Systemic administration, by either intravenous or intramuscular injection, has been used most frequently with some success. Among the problems inherent in this method of administration is that the interferon can come into contact with uninfected or nonmalignant cells and may cause unwanted side effects. Accordingly, the preferred approach would be to deliver interferon directly to the affected tissues or organs. In some cases, this can be accomplished by direct injection into the diseased site. In other cases, e.g., eye diseases and diseases like herpes genitalis, herpes labialis, herpes zoster and adenovirus induced keratitis and condyloma, all of which produce skin lesions, local topical application is the preferred method of administration. The present invention is concerned with this latter method of local administration.

The topical administration of interferon has proved to be a formidable problem for a number of reasons. First, interferon is a protein with a higher molecular weight than the molecular weights of therapeutic agents usually administered in topical preparations, e.g., porcaine, nitroglycerin, etc. In general, large molecular weight proteins have a much smaller solution diffusion coefficient than low molecular weight substances, a difference which generally becomes exacerbated in semi-solid media. Accordingly, the vehicle used to administer interferon locally must be able to hold the high molecular weight interferon in suspension during packaging, shipping and application, and yet also be able to release the interferon from the vehicle in a reasonable length of time once it has been applied at the diseased site. Second, the vehicle must not adversely affect the activity of the interferon by direct chemical action, precipitation or immobilization, any of which would preclude interaction of the interferon with the diseased site.

Third, and in many ways most difficult to achieve, the vehicle should allow the interferon preparation to have a sufficiently long shelf-life at room and body temperatures to allow for convenient shipping, handling and administration by the patient. In general terms, if a therapeutic agent is to be administered topically, the agent and its vehicle should satisfy the following shelf-life conditions: (1) the agent should retain a significant fraction of its therapeutic effect when held at room temperature (22° C.) for a period of approximately fourteen days; and (2) the agent should also retain a significant fraction of its activity when held at body temperature (37° C.) for a period of approximately one day. The fourteen day requirement at room temperature allows for shipping, handling and retailing of the preparation. The one day requirement at body temperature allows the patient to carry the product on his person and apply it throughout the day when needed.

Interferons produced by recombinant-DNA techniques or from natural sources when in a crude or partially purified form are notoriously temperature labile substances. For example, Moller, et al, reported at the Third Annual International Congress for Interferon Research that even at 4° C., a human leukocyte interferon gel lost 80% of its activity in just two weeks. (Moller, B. R., Johannesen, P., Osther, K., Ulmsteen, U., Hastrup, J. and Berg, K., "Initial Evaluation of Topical Treatment of Dysplasia of the Cervical Epithelum with a Human Leukocyte Interferon Gel", Third Annual International Congress for Interferon Research, 1982.) Plainly, this is far from the fourteen days at 22° C. and one day at 37° C. stability requirements which an interferon preparation should achieve to satisfy commercial requirements. Presently available data suggest that highly purified interferons, in particular, highly purified $\gamma$-interferon, may also be temperature labile. In view of this state of the art, it is clear that a vehicle for use in topically administering interferon has a heavy burden to carry in terms of providing a therapeutically stable preparation.

SUMMARY OF THE INVENTION

It is an object of the present invention to overcome the problems in the prior art regarding providing suitable vehicles for the topical administration of interferon. In particular, it is an object of the present invention to provide topical administration vehicles for interferon which will hold a high molecular weight interferon in suspension during packaging, shipping, and application and yet be capable of ready release of the active interferon at the diseased site. It is a further object of the invention, to provide interferon administration vehicles which do not significantly diminish the activity of the interferon by direct chemical action, precipitation, immobilization or other mechanisms, both during manufacture of the preparation and thereafter. It is an additional object of the invention to provide interferon administration vehicles in which the interferon exhibits an extended shelf life at both room and body temperatures. More particularly, it is an object of the invention to provide interferon administration vehicles in which the interferon maintains a substantial fraction of its biological activity for a period of approximately fourteen days or longer at room temperature and approximately one day or longer at body temperature.

In accordance with the invention, the foregoing and other objects are achieved by providing an interferon preparation to be administered topically comprising a therapeutically effective amount of one or more interferons, a vehicle base compatible with the interferon or interferons to be administered and an effective amount of a protease inhibitor for the purpose of reducing the rate of decay of the biological activity of the interferon or interferons due to proteolytic agents. In accordance with the preferred embodiments of the invention, the protease inhibitor is selected from the group consisting of $\alpha_1$-antitrypsin inhibitor, $\alpha_2$-macroglobulin, soybean inhibitor, $N^\alpha$-tosyl-L-lysine chloromethyl ketone, phenylmethylsulfonyl fluoride, $N^\alpha$-tosylphenylalanine chloromethyl ketone or mixtures thereof. A particularly preferred protease inhibitor is human $\alpha_1$-antitrypsin inhibitor. In accordance with other preferred embodiments of the invention, the interferon preparation includes an effective amount of one or more preservatives to prevent decay of interferon activity due to microbial agents.

In the case of vehicles in ointment form, e.g., pastes, creams, gels and the like, particularly preferred vehicle bases are those which include hydroxyethyl cellulose or are prepared from a mixture of polyethylene glycols. The hydroxyethyl cellulose bases provide especially high interferon titers. Also, interferon preparations employing these bases have been found to have a uniform consistency and a pleasing feel and appearance.

For vehicle bases using polyethylene glycols, a preferred method for manufacturing the finished preparation includes the steps of heating the polyethylene glycols to a temperature of approximately 45° C., heating the interferon or interferons to a similar temperature, mixing the heated polyethylene glycols and heated interferons together, and cooling the resulting mixture to room temperature or below. Interferon preparations formulated in this way have been found to be uniform and homogeneous, and to have high levels of interferon activity notwithstanding the fact that the procedure includes heating the interferon to a relatively high temperature.

DESCRIPTION OF THE PREFERRED EMBODIMENTS

As described above, the present invention relates to vehicles for the topical administration of interferon.

The invention is applicable to all types of interferons including natural interferons, interferons produced by recombinant DNA technology and interferons produced by chemical synthesis. Also, the invention can be used with crude, semi-purified and purified interferons.

Examples of the more common types of interferons with which the invention can be used include $\alpha$, $\beta$ and $\gamma$ interferons of human and animal origin. Each of these three types of interferons can be produced by a variety of techniques. For example, a method for producing $\alpha$-interferon is described by Cantell et at in *Methods in Enzymology*, Vol. 78, pages 29–38 (1981). Similarly, $\beta$-interferon production schemes are described by Leong and Horoszewicz in *Methods in Enzymology*, Vol. 78, pages 87–101 (1981), and by Van Damme and Billiau in *Methods in Enzymology*, Vol. 78, pages 101–119 (1981). A method for producing $\gamma$-interferon is described by Johnson et al in *Methods in Enzymology*, Vol. 78, pages 158–162 (1981). A particularly preferred method for producing $\gamma$-interferon is described in U.S. patent application Ser. No. 446,160, filed on Dec. 2, 1982, and assigned to the same assignee as the present invention. The pertinent portions of the foregoing references and patent application are incorporated herein by reference.

In general, interferon produced by these and other methods is supplied as a liquid. Such a liquid when used as a component of the topical vehicles of the present invention will be referred to herein as an "interferon source liquid."

The amount of interferon which is topically administered in any partiuclar case, as well as the frequency at which interferon is administered, will depend upon such factors as the interferon used, the disease being treated, the patient's response to interferon treatment, and whether the preparation used is a semi-solid (e.g., an ointment) or a liquid (e.g., an eyedrop, nosedrop, spray or douche).

For $\alpha$ and $\beta$ interferons, unit strengths have been established by the National Institutes of Health (United States Department of Health and Human Services, Bethesda, Md.). In terms of these unit strengths, dosage levels for ointment preparations using crude or partially purified natural interferons can range from about 10,000 NIH Units/gram of ointment to 1,000,000 NIH Units/gram, while for purified natural and recombinant DNA interferons, the dosage levels can be as high as 50,000,000 NIH Units/gram. Preferred dosage levels for $\alpha$ and $\beta$ interferons in ointments are generally between about 25,000 and about 500,000 NIH Units/gram of ointment.

The conveniently obtained dosage levels for liquid preparations exhibit a similar variability as a function of the source of the interferon used. Thus, a formulation including crude or partially purified natural $\alpha$ or $\beta$ interferons can have a strength of between approximately 25,000 and 2,000,000 NIH Units per milliliter of preparation, with a particularly preferred dosage level being between approximately 100,000 and 1,000,000 NIH Units per milliliter. If desired, even higher levels, e.g., 50,000,000 NIH Units/milliliter, can readily be obtained with purified natural and recombinant DNA interferons.

For $\gamma$-interferon, unit strengths have not yet been established. $\gamma$-interferon is commercially available from a number of sources, including Interferon Sciences, Inc., (New Brunswick, N.J.), the assignee of the present application, and Meloy Laboratories (Springfield, Va.). The strengths of these commercial preparations are given in units established by in-house standards. In terms of these units, ointment and liquid $\gamma$-interferon preparations generally contain similar concentration levels to those given above for α and β interferons.

In addition to administering one interferon at a time, the present invention is also applicable to the administration of mixtures of interferons, including interferons of different types, interferons from different sources, and interferons produced by different methods of manufacture. For example, it is known that α and γ interferons, as well as possibly other interferon combinations, e.g., mixing different recombinantly produced α-interferons, can have a synergistic effect. The present invention specifically encompasses the topical administration of such synergistic combinations.

The vehicle base used with the present invention must simultaneously satisfy the following criteria: (1) the vehicle base must be capable of holding the high molecular weight interferon or interferons in suspension and yet be able to release the interferon or interferons at the diseased site; (2) the vehicle base must be compatible with the interferon or interferons being administered so that the activity of the interferon is not adversely affected; (3) the vehicle base must be acceptable to the patient, i.e., it should be non-irritating, non-toxic and should have an appropriate odor, color and texture; and (4) the vehicle base must have suitable rheological properties so that it can be easily manufactured and dispensed into containers and subsequently applied to the diseased site by the patient.

For ointment type vehicles, various vehicle bases can be used with the present invention, including water soluble and water insoluble bases. In general, water soluble bases, e.g., bases including glycol ethers, celluloses, polyoxyl stearates, and the like, are preferred because of the proteinaceous character of interferons.

A particularly preferred water-soluble base for use with the present invention comprises a mixture of one or more polyethylene glycols. By combining different molecular weight polyethylene glycols, e.g., polyethylene glycols having molecular weights between 300 and 20,000, a wide range of viscosities and aqueous solution capacities (e.g., 15-25%) for this type of base can be obtained. One such formulation comprises a 60:40 mixture of a 400 molecular weight polyethylene glycol and a 3350 molecular weight polyethylene glycol. This mixture produces a particularly suitable vehicle base for administering interferons.

To use these polyethylene glycol-containing bases with interferons, however, requires special handling procedure for incorporating the interferon into the vehicle base. At room temperature and below, the various mixtures of polyethylene glycols suitable for use with the present invention are semi-solid pastes, rather than liquids. In contrast, interferons, as stated above, are typically supplied as liquids. The two components can be combined by mechanical mixing, but such mixing often results in a non-homogenous ointment and can denature the interferon. In accordance with the invention, and as described in more detail in connection with the examples presented below, it has been found that a superior polyethylene glycol-based ointment can be prepared by combining the interferon with the polyethylene glycols when both components have been heated to an elevated temperature, e.g., 45° C.. Surprisingly, it has been found that this procedure does not significantly deactivate the interferon, notwithstanding its proteinaceous character, which one would expect would lead to heat sensitivity.

In order to maintain the consistency of the final preparation within a suitable range for application to the diseased site, it has been found that the amount of interferon source liquid added to the polyethylene glycol vehicle bases, such as, the 60:40 base described above, should be kept in the range of from about 0.01 to 0.25 milliliters per gram of base, and most preferably in the range from about 0.05 to 0.15 milliliters per gram of base.

Another particularly preferred water-soluble vehicle base for use with the present invention employs hydroxyethyl cellulose as a thickening agent for the ointment. This thickening agent is particularly useful in preparing an interferon ointment because the agent does not completely thicken the ointment immediately, but only after a period of approximately 2-4 hours. Accordingly, the interferon can be mixed with the hydroxyethyl cellulose-containing vehicle base while the base still has a relatively low, liquid-like, viscosity. Since, as discussed above, interferons are normally supplied as liquids, this means that a homogeneous mixture can be easily obtained. Also, it has been found that hydroxyethyl cellulose-containing vehicle bases, after they fully gel, give the final preparation a pleasing feel and appearance. Moreover, interferon preparations using this vehicle base suprisingly have been found to have especially high interferon titers.

A preferred ointment base using hydroxyethyl cellulose includes between about 1 and 5 weight percent of hydroxyethyl cellulose having, for example, a viscosity of 2200 centipoise, between about 10 and 50 weight percent of glycerin and between about 49 and 85 weight percent of water. To this vehicle base is perferably added between about 10 and 30 milliliters per hundred grams of base of interferon source liquid. A particularly preferred hydroxyethyl cellulose vehicle base includes between about 2 and 3 weight percent of hydroxyethyl cellulose (2200 centipoise viscosity), between about 20 and 38 weight percent of glycerin and between about 60 and 78 weight percent of water. In combination with this base, preferably between about 15 and 20 milliliters of interferon source liquid are used per hundred grams of base. For interferon source liquids having low titers, the quantity of water used in the vehicle base can be reduced and higher amounts of source liquid can be admixed with the base. In this way, the titer of the final preparation can be adjusted without adversely affecting the preparation's rheological properties. In place of glycerin, the hydroxyethyl cellulose-containing vehicle base can include polysorbate and other similar wetting agents. Instead of hydroxyethyl cellulose, other celluloses and their derivatives, such as methylcellulose, carboxymethyl cellulose and hydroxypropyl cellulose, can be used.

For liquid type vehicles, e.g., drops, sprays or douches, the vehicle base is a non-irritating liquid which is compatible with the interferon or interferons being administered. In general, aqueous solutions are preferred because of the proteinaceous character of interferons. Examples of preferred liquid bases include physiological saline, 5-50% glycerin in water and 5-50% sorbitol in water. Of these bases, physiological saline is most preferred because it is isotonic and almost always non-irritating to the patient.

To enhance the wettability of the vehicle base, various known wetting agents, such as a polysorbate surfactant, can be used. Also, the viscosity of the preparation can be adjusted using various known viscosity modifiers, such as polyvinyl alcohol.

As discussed above, for liquid type vehicles, interferon dosage levels are generally between approximately 25,000 and 50,000,000 units per milliliter, depending on the source of the interferon used in the preparation. As will be evident to those skilled in the art, these dosage levels, as well as any other desired dosage levels, are easily achieved by varying the relative amounts of interferon source liquid and vehicle base.

In addition to an interferon component and a vehicle base component, the topical preparations of the present invention may also include one or more protease inhibitors. These inhibitors are included in the preparations for the purpose of reducing the rate of decay of the biological activity of the interferon component due to proteolytic agents found in crude and partially purified preparations. In accordance with the invention, it has been found that the major source of interferon decay in such topical preparations, especially at elevated temperatures, i.e,. room or body temperature, is digestion of the interferon by proteolytic enzymes introduced into the preparation as part of the interferon source liquid. Once in the preparation, these contaminating enzymes, over time, destroy the therapeutic potency of the interferon.

The proteolytic enzymes found in interferon source liquids come from the human serum, leukocytes or other biological materials used to manufacture the interferon, as well as possibly from contaminating microorganisms. Typically these enzymes are of the "serine" protease type, in that, they have a critical serine residue at their active site. Examples of such proteolytic enzymes include trypsin, plasmin, thrombin, leukocyte elastase, kallikrien and cathepsin. In some cases (e.g., plasmin and thrombin), the interferon source liquid may not actually include the active proteolytic enzyme, but rather, an inactive precursor which is slowly converted to the active form, especially at elevated temperatures.

To control the effects of these proteolytic enzymes, the topical preparations of the present invention include one or more protease inhibitors which interact with the proteolytic enzymes and prevent them from digesting and thus inactivating the interferon in the interferon source liquid.

Various proteolytic inhibitors of human, animal or plant origin can be used in the practice of the present invention. Because of the highly conserved nature of both protease inhibitors and the active sites of the proteolytic enzymes typically present in interferon source liquids, the inhibitor need not be from the same species as the proteolytic enzyme, but can be from a different species or even of plant origin. For example, a soybean trypsin inhibitor (also referred to herein as "soybean inhibitor" and abbreviated "STI") is capable of inhibiting trypsins from such diverse sources as humans, cows, salmon, stingrays, barracudas and turkeys. Also, in addition to inhibiting trypsins, STI will inhibit bovine and chicken chymotrypsin, human plasmin, human kallikrien and cocoonase, as well as blocking the conversion of prothrombin to thrombin.

Protease inhibitors particularly preferred for use with the present invention include STI, $\alpha_1$-antitrypsin inhibitor (hereinafter abbreviated "$\alpha_1$-AT"), N$^\alpha$-tosyl-L-lysine chloromethyl ketone (hereinafter abbreviated "TLCK"), phenylmethylsulfonyl fluoride (hereinafter abbreviated "PMSF"), N$^\alpha$-tosylphenylalanine chloromethyl ketone (hereinafter abbreviated "TPCK"), $\alpha_2$-macroglobulin, and mixtures thereof. Of these inhibitors, STI is particularly preferred because of its low cost and $\alpha_1$-AT is most preferred, especially when prepared from human serum, because of the reduced chance of allergic reactions. A suitable technique for purifying human $\alpha_1$-AT is described by J. Travis and D. Johnson in *Methods in Enzymology*, Vol. 80, pages 754–765, the pertinent portions of which are incorporated herein by reference. The other preferred protease inhibitors listed above are commercially available from various sources including Sigma Chemical Company, St. Louis, Mo. (STI, TLCK and PMSF), Chemical Dynamics Corp., South Plainfield, N.J. (TPCK), and Boehringer Mannheim Biochemicals, Indianapolis, Ind. ($\alpha_2$-macroglobulin).

The amount of protease inhibitor included in the topical preparation depends upon the amount and type of proteolytic enzyme present in the interferon source liquid, and the particular inhibitor used. For example, crude $\alpha$-interferon sold by Interferon Sciences, Inc., (New Brunswick, N.J., Catalog #1100), and then concentrated as described below in Example 1 (hereinafter referred to as "crude concentrated $\alpha$-interferon source liquid"), typically contains approximately 100 mg of protein per milliliter of liquid. Of this 100 milligrams, up to 1% may be proteolytic enzymes, generally of the type found in human plasma (e.g., thrombin, plasmin, etc.). These enzymes have molecular weights in the range of 25,000 to 100,000 daltons. In comparison, STI, for example, has a molecular weight of approximately 20,000 daltons. Accordingly, since this inhibitor generally forms a 1:1 complex with its target proteolytic enzymes, the addition of 1 mg of inhibitor per milliliter of interferon source liquid can be expected to produce a multifold molar excess of inhibitor. In practice, as described in detail in Examples 5 and 6 below, it has been found that a level of STI on the order of 0.25 milligrams per milliliter of crude concentrated $\alpha$-interferon source liquid is sufficient to guarantee an extended interferon half-life, especially at elevated temperatures, such as 37° C. Since this particular interferon source liquid has an activity of approximately $2 \times 10^6$ Units per milliliter and since it is preferable to have between 25,000 and 500,000 Units per gram of ointment, this means an STI addition rate of between approximately 0.003 and 0.06 milligrams of inhibitor per gram of ointment. ([25,000 Units/gram]/[$2 \times 10^6$ Units/ml]$\times$[0.25 mg.ml]=0.003 mg/gm; [500,000 Units/gram]/[$2 \times 10^6$ Units/ml]$\times$[0.25 mg.ml]=0.06 mg/gm). Similarly, for a liquid preparation using this particular interferon source liquid and having a strength of between 200,000 and 2,000,000 Units per milliliter of preparation, between approximately 0.025 and 0.25 milligrams of this inhibitor is used per milliliter of solution. ([200,000 Units/ml]/[$2 \times 10^6$ Units/ml]$\times$[0.25 mg/ml]=0.025 mg/ml; [2,000,000 Units/ml]/[$2 \times 10^6$ Units/ml]$\times$[0.25 mg/ml]=0.25 mg/ml).

As will be evident to persons of ordinary skill in the art, a similar procedure to that described above can be used to determine the appropriate addition levels for other inhibitors and other interferon source liquids.

In addition to including one or more interferons and a vehicle base, the interferon preparations of the present invention can include various optional components. For example, it is generally desirable to include one or more preservatives in the preparation to prevent microbial growth. Examples of preservatives which have been found compatible with interferons include benzolkonium chloride and methyl and propyl parabens. Also, the preparations can include noninterferon type therapeutic agents in addition to the one or more interferons. Other optional components which can be included in the preparation are various coloring agents and protein stabilizing agents, such as, glycerol, surcrose, sorbitol and mannitol.

Without intending to limit it in any manner, the present invention will be more fully described by the following examples. In certain of the examples, activities are reported for interferon-containing ointment preparations. These activities were determined by the following procedure. First, a measured amount of the ointment was placed in a suitable container, such as, a centrifuge tube, and a measured amount, e.g., 50 ml., of 4° C. sterile phosphate buffered saline (pH 7.4) was added to the container. The container was then vortexed and placed in a 4° C. environment to allow the ointment sample to dissolve in the phosphate buffered saline. Titers were then calculated using samples of the ointment-containing phosphate buffered saline at 0 dilution and 1/10 dilution. When percentage activity data were desired, these data were determined by comparing the measured titers with the expected titer for the interferon originally used in preparing the ointment, assuming a uniform distribution of the interferon in the ointment and using a dilution factor corresponding to the concentration of the interferon in the ointment and the dilution due to the addition of phosphate buffered saline. Also, when half-life data were desired, these data were calculated using the decay constants obtained from a linear least squares regression analysis of the log of percent theoretical activity versus time.

EXAMPLE 1

Preparation of Crude Concentrated α-Interferon Source Liquid

Crude concentrated α-interferon source liquid was prepared from Natural Crude α-Interferon sold by Interferon Sciences, Inc., (New Brunswick, N.J., Catalog #1100) as follows. The pH of the commercial product was checked and, if necessary, adjusted to 7.0-7.2 using sodium hydroxide. The pH adjusted material was then concentrated using a hollow fiber filter having a 10,000 molecular weight cutoff and run at 20 p.s.i., until the volume of the product was 1/50 of the starting volume. The concentrated product was then clarified by centrifugation at 18–20,000×g, and finally sterile filtered.

EXAMPLE 2

Preparation of an Interferon Stock Solution

An interferon stock solution was prepared having the following composition:

|  |  | Volume % |
|---|---|---|
| 10X | Phosphate Buffered Saline | 10.0 |
| 10% | Polyvinyl Alcohol | 10.0 |
| 3% | Polysorbate 80 | 10.0 |
| 0.5% | Benzolkonium Chloride | 2.0 |
|  | Crude concentrated α-IFN (Ex. 1) | 68.0 |

The 10X phosphate buffered saline was prepared by dissolving sodium chloride (1.5M), potassium chloride (70 mM), monobasic potassium phosphate (200 mM) and dibasic sodium phosphate (200 mM) in purified water. The pH of the solution was adjusted to 7.4±0.2 with concentrated sodium hydroxide and the final solution was sterile filtered.

The 10% polyvinyl alcohol solution was prepared by mixing purified water with polyvinyl alcohol having a molecular weight of 10,000 (Aldrich, Milwaukee, Wis.). Because a 10% solution of polyvinyl alcohol having this molecular weight cannot be sterile filtered, the solution was prepared by mixing two thirds of the total volume of purified water with the polyvinyl alcohol, autoclaving this mixture, and then adding the remaining one third of purified water, which had been sterile filtered.

The polysorbate 80 solution was prepared by mixing Tween 80 (Sigma, St. Louis, Mo.) with purified water and then sterile filtering the final solution. Similarly, the 0.5% benzolkonium chloride solution was prepared by mixing benzolkonium chloride with purified water and then sterile filtering the final solution.

The final interferon stock solution was simply prepared from its components by mixing those components under a sterile hood and then sterile filtering the resulting solution.

The stock solution has a viscosity and wettability appropriate for use as a liquid interferon preparation to be administered in the form of drops or a spray. Also, as illustrated below in Example 4, the stock solution can be conveniently used in the preparation of ointments employing hydroxyethyl cellulose as a vehicle base.

EXAMPLE 3

Preparation of an Interferon Ointment Having a Polyethylene Glycol Vehicle Base

An interferon ointment having a polyethylene glycol vehicle base was prepared as follows.

Sixty grams of polyethylene glycol 400 liquid and 40 grams of polyethylene glycol 3350 powder, both obtained from Fisher Scientific, Fair Lawn, N.J., were mixed together in a sterile glass beaker and then autoclaved at 121° C. for 40 minutes. While still molten, the beaker was submerged into a 50° C. water bath set inside a laminar flow hood, The mixture was slowly stirred with a sterile propeller-type stirring blade and its temperature was adjusted to approximately 45° C. Fifteen milliliters of frozen crude concentrated α-interferon source liquid, prepared in accordance with Example 1 above, was thawed at 4° C. and then heated in a water bath to a temperature of approximately 45° C. The interferon was then added to the molten polyethylene glycol mixture and the two components stirred together until the mixture was homogeneous and had an even color.

Using a syringe and a pipet, aliquots of the interferon/polyethylene glycol mixture were placed in sterile aluminum ointment tubes, which had been prechilled to 4° C. The open ends of the tubes were covered with alcohol swabbed parafilm, and the tubes were placed in a −20° C. freezer. After approximately 20 minutes at −20° C., the tubes were crimped under a laminar flow hood.

To fill a large number of tubes, it has been found preferable to perform the filling step in batches so as to minimize the amount of time during which the ointment stands at room temperature.

Figure 1:
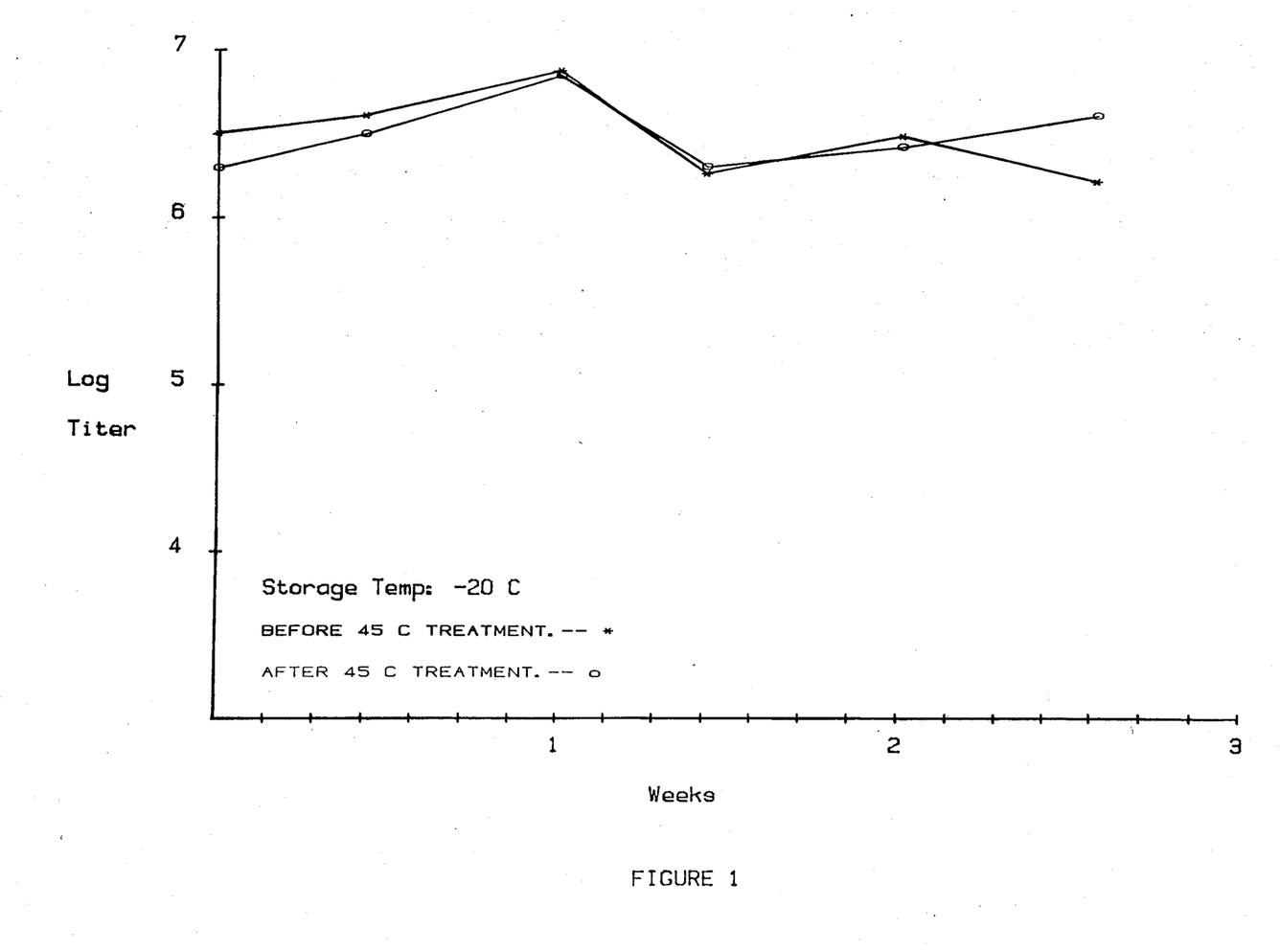
FIG. 1 shows the storage behavior at −20° C. of $\alpha$-interferon preparations which have and have not been heated to 45° C.

To demonstrate that the heating of the interferon source liquid to 45° C. to facilitate its mixing with the polyethylene glycol mixture did not significantly decrease the activity of the interferon, a sample of crude concentrated α-interferon source liquid, prepared in accordance with Example 1, was heated to 45° C., held at that temperature for 1 hour, and then stored at −20° C. The changes in the titer of this sample over time were compared to those of an unheated sample. The results are shown in FIG. 1. As demonstrated by this figure, the titers of the heated and unheated interferon samples are essentially identical, thus establishing that the heating step used to prepare polyethylene glycol-based ointments does not destroy the biological activity of the interferon.

To compare the quality of an ointment produced by mixing the interferon and the polyethylene glycols at elevated temperature with the quality of an ointment produced by mechanical mixing of these components at room temperature, a batch of ointment was prepared by adding 45 milliliters of crude concentrated α-interferon source liquid to 300 grams of the 60:40 polyethylene glycol mixture, described above, which had been cooled to room temperature. The two components were placed in a sealable plastic bag and the contents were mixed by kneading the bag by hand and rolling the bag using a cylindrical bar. The kneading and rolling was carried out for a period of approximately 30 minutes, after which the ointment was compared with the ointment prepared by heating, as described above. The mechanically mixed ointment was in general found to have a non-uniform color and consistency indicating that a homogeneous dispersion of the interferon throughout the polyethylene glycol mixture had not been achieved. In comparison, the ointment prepared by heating the interferon and the polyethylene glycols exhibited uniform color and consistency throughout the ointment.

EXAMPLE 4

Preparation of an Interferon Ointment Having a Hydroxyethyl Cellulose Vehicle Base An interferon ointment having a hydroxyethyl cellulose vehicle base was prepared as follows.

First, 0.96 grams of high viscosity (2200 centipoise) hydroxyethyl cellulose manufactured by Polysciences Warrington, Pa., Catalog #05568) were measured into a beaker. Aggregates of the hydroxyethyl cellulose powder were broken up. Next, 7.67 grams of USP glycerin were added to the hydroxyethyl cellulose powder and the two components were mixed to form a uniform slurry. Then, 24.5 milliliters of purified water were added to the hydroxyethyl cellulose/glycerin mixture. The water was added as fast as possible without stirring. Thereafter, the solution was mixed rapidly until the gel thickened.

The vehicle base mixture was then autoclaved at 121° C. for 40 minutes. A manual slow exhaust cycle was used at the end of autoclaving so that the pressure was reduced to zero slowly to avoid any overflow of the material upon decompression. Under a laminar flow hood, the autoclaved mixture was cooled to between 60° C. and 70° C., with mixing. At this temperature, 0.023 grams of propyl paraben and 0.96 grams of methyl paraben were added to the gel. Care was taken to insure that the mixture did not reach a temperature above about 70° C. so as not to inactivate the propyl and methyl parabens. The parabens were mixed with the vehicle base until no paraben powder was observed in the mixture. The vehicle base/paraben mixture was then placed in an ice bath and cooled, with mixing, until a temperature of 4° c. was reached.

Five milliliters of the sterile-filtered interferon stock solution prepared in accordance with Example 2 above were then combined with 0.2 milliliters of a 50 mg/ml, sterile-filtered, soybean trypsin inhibitor solution (Sigma Chemical Company, St. Louis, Mo.). This solution was then added to the cooled vehicle base/paraben mixture and the combination was mixed until a uniform dispersion was visually observed. The gel was then transferred to sterile syringes by removing the plungers from the syringes and adding the gel to the barrel of the syringes using a sterile spatula. The dispensing ends of the syringes had been previously closed with sterile, heat-sealed hubs. The barrel openings of the syringes were then parafilmed with two layers of parafilm. The heat-sealed hubs were transferred to a refrigerated centrifuge. The syringes were then centrifuged at 4° C. for 15 minutes at 2,000 rpm to remove encapsulated air from the gel.

After centrifuging, the tape and parafilm, but not the hubs, were removed from the syringes under a hood. Plungers were placed into the syringes and the hubs replaced with sterile dispensing cannulas. Using the syringes, the gel was then dispensed into sterile aluminum ointment tubes, which were then crimped closed.

These procedures were found to produce uniform ointments having an excellent consistency for topical application. Scaling up of these procedures to larger quantities was found to produce ointments having the same excellent uniformity and consistency.

To illustrate the increased titers obtained using hydroxyethyl cellulose bases, as opposed to polyethylene glycol bases, a series of ointments of each type were prepared and their titers measured at various times during storage at −20° C. The hydroxyethyl cellulose containing ointments were prepared in accordance with the procedures described in this example, except that the crude concentrated α-interferon source liquid of Example 1 was used in place of the interferon stock solution of Example 2, and soybean trypsin inhibitor was not included in the preparation. The results of these experiments are shown in Table 1, where the second column gives the theoretical titer of the ointment in Units per gram based on the amount and known titer of the interferon source liquid used to prepare the ointment, the third column gives the storage duration in days, the fourth column gives the number of assays conducted during the storage interval, and the last column gives the average of those assays expressed as a percentage of the theoretical titer. As shown in this table, preparation and storage of the hydroxyethyl cellulose-based ointment resulted in essentially no loss in interferon activity.

TABLE 1

| | Titers of HEC Ointments Stored at −20° C. | | | |
|---|---|---|---|---|
| Expt. | Theo. Titer (U/gm) | Storage Duration | No. of Assays | % Theo. Titer |
| 1 | 163,000 | 177 days | 11 | 141 |
| 2 | 194,000 | 63 days | 11 | 100 |
| 3 | 198,000 | 56 days | 12 | 114 |
| 4 | 599,940 | 72 days | 9 | 102 |

The polyethylene glycol containing ointments were prepared from the concentrated α-interferon stock solution of Example 1, using the mechanical (Expts. 1-3) and heated (Expts. 4-15) mixing procedures described in Example 3. Before being added to the polyethylene glycol base, the interferon stock solutions for Expts. 10-15 were modified as follows: in Expt. 10, sodium chloride was added to the stock solution until a 5M concentration was obtained; in Expt. 11, 20% glycerol (v/v) was added; in Expt. 12, 0.13% benzolkonium chloride (w/v) was added; in Expt. 13, 0.25% methyl paraben (w/v) and 0.06% propyl paraben (w/v) were added; in Expt. 14, 0.13% benzolkonium chloride (w/v), 0.25% methyl paraben (w/v), and 0.06% propyl paraben (w/v) were added; and in Expt. 15, 1% polyvinyl alcohol (w/v), 0.3% Tween 80 (v/v) and 0.01% benzolkonium chloride (w/v) were added. These additives were included in the hope of imparting stability to the ointment at elevated temperatures, e.g., 22° C. and 37° C. It was found that none of these modifications produced the desired stability and it was only through the addition of protease inhibitors as discussed above and illustrated below in Examples 5 and 6 that high temperature stability of interferon preparations could be achieved.

Both the modified and unmodified polyethylene glycol-containing ointments were stored at −20° C. and assayed in the same manner as the hydroxyethyl cellulose-containing ointments. The data for these samples are given in Table 2. A comparison of these data with those for the hydroxyethyl cellulose containing ointments shows the clear superiority of the hydroxyethyl cellulose base. When combined with a hydroxyethyl cellulose base, the interferon lost essentially none of its activity; when combined with a polyethylene glycol base, as shown by the last column in Table 2, the interferon lost on average 34% of its activity. It is of interest to note that the interferon lost activity not only for the heated mixing procedure (Expts. 4-15), but also for the mechanical mixing procedure (Expts. 1-3). This further supports the conclusion drawn from the data of FIG. 1 that heating of the interferon source liquid so that it can be readily combined with a polyethylene glycol base does not, in itself, cause deactivation of the interferon.

Although the polyethylene glycol based ointments do exhibit reduced titers when measured against hydroxyethyl cellulose based ointments, it should be noted that interferon does retain a substantial fraction of its activity in these ointments. In certain cases, polyethylene glycol based ointments will be preferred because of their extensive use and acceptance by the medical community.

TABLE 2

Titers of PEG Ointments Stored at −20° C.

| Expt. | Theo. Titer (U/gm) | Storage Duration | No. of Assays | % Theo. Titer |
|---|---|---|---|---|
| 1 | 217,000 | 47 days | 7 | 51.9 |
| 2 | 315,000 | 47 days | 6 | 74.0 |
| 3 | 571,000 | 47 days | 7 | 31.4 |
| 4 | 219,000 | 98 days | 10 | 62.2 |
| 5 | 166,000 | 96 days | 10 | 57.6 |
| 6 | 207,000 | 18 days | 7 | 113.5 |
| 7 | 198,000 | 153 days | 10 | 66.3 |
| 8 | 238,000 | 21 days | 7 | 105.0 |
| 9 | 466,000 | 70 days | 10 | 41.6 |
| 10 | 166,000 | 96 days | 10 | 44.9 |
| 11 | 166,000 | 96 days | 9 | 44.5 |
| 12 | 238,000 | 33 days | 9 | 74.5 |
| 13 | 238,000 | 153 days | 10 | 88.9 |
| 14 | 238,000 | 33 days | 9 | 53.5 |
| 15 | 162,000 | 25 days | 10 | 81.0 |

EXAMPLE 5

Effects of Protease Inhibitors on a Liquid Interferon Preparation

This example demonstrates that an effective amount of a protease inhibitor will reduce the rate of decay of the biological activity of a liquid-type interferon preparation.

Ten milliliters of the interferon stock solution described in Example 2 was divided into three equal parts. Solid soybean trypsin inhibitor (Sigma Chemical Company, St. Louis, Mo.) was added to one of the aliquots at a concentration of 1 mg/ml and to a second of the aliquots at a concentration of 10 mg/ml. The third aliquot received no STI. Each aliquot as stored at 22° C. and assayed in an identical manner at various points in time over a four to five week period. The titer of the interferon stock solution on day 0 was approximately $1 \times 10^6$ U/ml.

Figure 2:
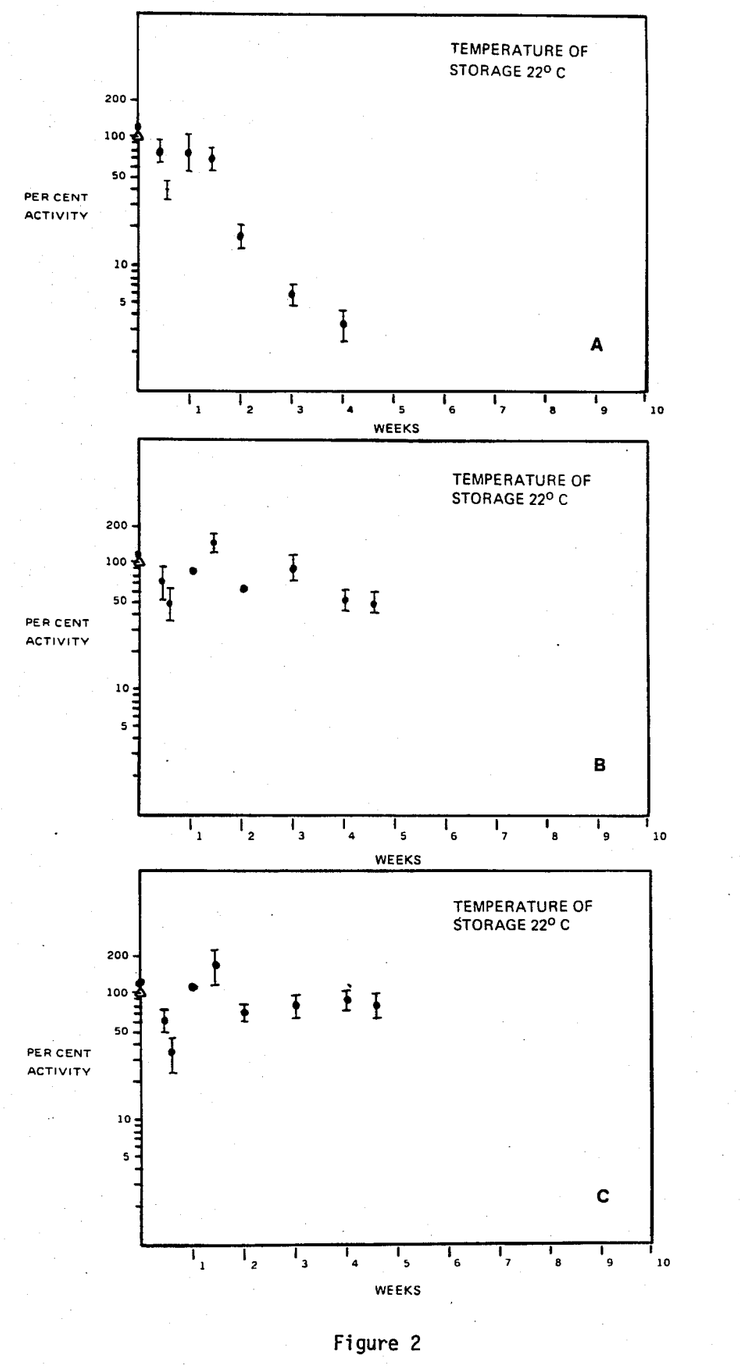
FIG. 2 shows the effects of 0 mg/ml (panel A), 1 mg/ml (panel B) and 10 mg/ml (panel C) of soybean inhibitor on a liquid interferon preparation stored at 22° C.

The results of this experiment are shown in FIG. 2, where panel A shows the percent activities over time of the solution which contained no STI, panel B shows the percent activities of the solution which contained 1 mg/ml STI, and panel C shows the present activities of the solution which contained 10 mg/ml STI. As shown by these data, the solution containing no STI essentially lost all of its activity within four weeks. In contrast, the solution containing 1 mg/ml STI maintained a significant fraction (e.g., approximately 50% of its original activity) over the same period of time. With the even higher STI level of 10 mg/ml, the solution essentially maintained most of its original biological activity, the activity at 4 to 5 weeks being more than 80% of the original activity.

These data plainly establish the effectiveness of a protease inhibitor in stabilizing an interferon-containing topical preparation so that the preparation can be stored for extended periods of time at room temperature.

EXAMPLE 6

Effects of Protease Inhibitors On Ointment Type Interferon Preparations

To demonstrate the enhanced temperature stability of interferon ointment preparations resulting from the incorporation of a protease inhibitor therein, a series of ointments was prepared having various protease inhibitors at various concentrations. The results are shown in Table 3. The method of preparation of the various ointments and the storage conditions the ointments were subjected to were as follows.

In Experiments 1-4, an interferon stock solution was prepared as described in Example 2 using the crude concentrated α-interferon source liquid described in Example 1. Various amounts of STI in solid form were added to this interferon stock solution. The STI-containing stock solution was combined with the hydroxyethyl cellulose vehicle base of Example 4, which, as described in Example 4, included 0.025% and 0.06% (w/v) of methyl and propyl paraben, respectively. All interferon containing solutions were kept at 4° C. prior to use, and the mixing with the hydroxyethyl cellulose vehicle base was also performed at 4° C. As indicated above, the various components making up the interferon stock solution, as well as the resulting stock solution, were sterile filtered prior to use in formulating the interferon preparation. The finished gel was dispensed into ointment tubes and stored at the various temperatures listed in Table 1, i.e., −20° C., 4° C., 22° C., and 37° C..

The ointments used in Experiments 5-7 were prepared in the same manner as the ointments in Experiments 1-4, except that rather than using the interferon stock solution, the crude concentrated α-interferon prepared in accordance with Example 1 was directly combined with the protease inhibitor, and that resulting solution was combined with the hydroxyethyl cellulose vehicle base to which has been added methyl and propyl paraben in the concentrations given above.

As shown in Table 3, at −20° C. and 4° C. the interferon ointment preparations were stable irrespective of whether they had a protease inhibitor or not and irrespective of the amount and type of inhibitor used. The time periods given in parentheses for the −20° C. and 4° C. storage conditions represent the amount of time for which the ointment had been stored with no decay in biological activity being detectable.

At 22° C., the importance of having a protease inhibitor becomes evident. For Experiment 1, the ointment only had a half-life of 7.5 days, which is not long enough to provide convenient shipping, handling and dispensing to the patient. In contrast, the use of as little as 0.29 milligrams of STI per milliliter of crude concentrated α-interferon source liquid produced a half-life in the 30 day range. Similar half-lives were obtained with higher concentrations of STI and essentially no decay was achieved with concentrations of 12.5 milligrams per milliliter and 12.5 milligrams per milliliter of $\alpha_1$-AT and TLCK, respectively.

At 37° C., the importance of having a protease inhibitor in the ointment preparation is even more striking. With no inhibitor, the half-life of the α-interferon in the preparation was only 6 hours, plainly not long enough for the patient to conveniently carry the ointment with him and dispense it throughout the day. With increasing amounts of STI, this half-life increased steadily from 52.5 hours up to 154 hours, i.e., over 6 days, at a concentration of 29 milligrams of STI per milliliter of crude concentrated α-interferon source liquid. Similarly, with 12.5 milligrams of $\alpha_1$-At per milliliter of crude concentrated α-interferon source liquid and 12.5 milligrams of TLCK per milliliter of crude concentrated α-interferon source liquid, half-lives of 93 hours and 249 hours, respectively, were achieved. Again, these half-lives make it practical for a patient to carry the ointment with him and apply it at various times throughout the day.

As plainly shown by the data in Table 3, the inclusion of a protease inhibitor in an interferon ointment preparation markedly reduces the rate of decay of the biological activity of the interferon in the preparation.

Although specific embodiments of the invention have been described and illustrated, it is to be understood that modifications can be made without departing from the invention's spirit and scope. For example, although the invention has been illustrated with reference to α-interferon it is equally applicable to other types of interferon. Similarly, although the specific protease inhibitors STI, $\alpha_1$-At and TLCK have been used in the examples, the invention can be practiced with other protease inhibitors.

TABLE 3

ENHANCEMENT OF INTERFERON OINTMENT TEMPERATURE STABILITY USING PROTEASE INHIBITORS

| Experiment | 1 | 2 | 3 | 4 | 5 | 6 | 7 |
|---|---|---|---|---|---|---|---|
| Units of Interferon Per Milliliter of Crude Concentrated α-Interferon Source Liquid | $1.8 \times 10^6$ | $1.8 \times 10^6$ | $1.8 \times 10^6$ | $1.8 \times 10^6$ | $1.8 \times 10^6$ | $1.5 \times 10^6$ | $1.5 \times 10^6$ |
| Milliliters of Crude Concentrated α-Interferon Source Liquid Per Gram of Ointment | 0.088 | 0.088 | 0.088 | 0.088 | 0.131 | 0.125 | 0.125 |
| Amount of Inhibitor Per Milliliter of Crude Concentrated α-Interferon Source Liquid | None | 0.29 mg of STI | 2.9 mg of STI | 29 mg of STI | 3.98 mg of $\alpha_1$-AT | 12.5 mg of $\alpha_1$-AT | 12.5 mg of TLCK |
| Half-Life at −20° C. | No Decay (2 Months) | No Decay (2 Months) | No Decay (1.5 Months) | No Decay (1 Month) | No Decay (1 Month) | No Decay (1 Month) | No Decay (1 Month) |
| Half-Life at 4° C. | No Decay (2 Months) | No Decay (2 Months) | No Decay (1.5 Months) | No Decay (1 Month) | No Decay (1 Month) | No Decay (1 Month) | No Decay (1 Month) |
| Half-Life at 22° C. | 7.5 Days | 33 Days | 28 Days | 31 Days | 27 Days | No Decay (1 Month) | No Decay (1 Month) |
| Half-Life at 37° C. | 6 Hours | 52.5 Hours | 112 Hours | 154 Hours | 125 Hours | 93 Hours | 249 Hours |

What is claimed is:

1. An interferon preparation to be administered topically to a patient suffering from a disease which responds therapeutically to interferon comprising:
   (a) one or more interferons, the amount of the one or more interferons being sufficient to therapeutically affect the disease from which the patient is suffering;
   (b) a vehicle base compatible with the interferon or interferons being administered; and
   (c) an effective amount of one or more protease inhibitors for the purpose of reducing the rate of decay of the biological activity of the interferon or interferons due to proteolytic agents.

2. The interferon preparation of claim 1 wherein the protease inhibitors are selected from the group consisting of $\alpha_1$-antitrypsin inhibitor, $\alpha_2$-macroglobulin, soybean inhibitor, $N^\alpha$-tosyl-L-lysine chloromethyl ketone, phenylmethylsulfonyl fluoride, $N^\alpha$-tosylphenylalanine chloromethyl ketone and mixtures thereof.

3. The interferon preparation of claim 2 wherein the protease inhibitor is human $\alpha_1$-antitrypsin inhibitor.

4. The interferon preparation of claim 1 wherein the effective amount of one or more protease inhibitors produces a half-life for the interferon or interferons of at least fourteen days at 22° C.

5. The interferon preparation of claim 1 wherein the effective amount of one or more protease inhibitors produces a half-life for the interferon or interferons of at least one day at 37° C.

6. The interferon preparation of claim 1 wherein the vehicle base includes hydroxyethyl cellulose.

7. The interferon preparation of claim 1 wherein the vehicle base includes polyethylene glycol.

8. The interferon preparation of claim 1 further including an effective amount of one or more antimicrobial preservatives.

9. An α-interferon preparation to be administered topically to a patient suffering from a disease which responds therapeutically to α-interferon comprising:
(a) one or more α-interferons, the amount of said one or more α-interferons being sufficient to therapeutically affect the disease from which the patient is suffering; and
(b) a vehicle base compatible with the α-interferon or α-interferons being administered which includes hydroxyethyl cellulose as a thickening agent.

10. The α-interferon preparation of claim 9 further including an effective amount of one or more protease inhibitors for the purpose of reducing the rate of decay of the biological activity of the interferon or α-interferons due to proteolytic agents.

11. The α-interferon preparation of claim 9 further including an effective amount of one or more antimicrobial preservatives.

* * * * *